United States Patent [19]

Suovaniemi et al.

[11] 4,452,902
[45] Jun. 5, 1984

[54] METHOD AND EQUIPMENT FOR THE MEASUREMENT OF PROPERTIES OF A LIQUID

[75] Inventors: Osmo A. Suovaniemi; Pertti Ekholm; Johan Järnefelt, all of Helsinki; Esko Kaukanen, Espoo; Paul Partanen, Helsinki, all of Finland

[73] Assignee: Labsystems Oy, Finland

[21] Appl. No.: 323,102

[22] Filed: Nov. 19, 1981

[51] Int. Cl.³ .................. G01N 21/82; G01N 33/54
[52] U.S. Cl. .................. 436/517; 356/427; 422/72; 422/73; 436/34; 436/45; 436/164; 436/805
[58] Field of Search .............. 23/230 B, 915; 422/58, 422/73, 102, 72; 356/246, 427, 434, 436, 440, 442, 444, 39; 436/518, 805, 34, 45, 164, 517

[56] References Cited

U.S. PATENT DOCUMENTS

| | | | |
|---|---|---|---|
| 3,520,609 | 7/1970 | Lion | 356/39 |
| 3,682,586 | 8/1972 | Ertingshausen et al. | 436/34 |
| 3,999,862 | 12/1976 | Revillet et al. | 356/427 |
| 4,224,405 | 9/1980 | Hijikata | 436/34 X |
| 4,232,970 | 11/1980 | Sawamura et al. | 356/39 |
| 4,316,872 | 2/1982 | Rahm et al. | 422/72 X |

FOREIGN PATENT DOCUMENTS 3033870 4/1981 Fed. Rep. of Germany ........ 422/73

Primary Examiner—Arnold Turk
Attorney, Agent, or Firm—Hopgood, Calimafde, Kalil, Blaustein & Judlowe

[57] ABSTRACT

Method and apparatus for the measurement of properties of a liquid present in a vessel (2), for example for the measurement of the absorbance of a liquid, of the properties of an agglutination, precipitate (4) or any other reaction result placed on the bottom of a vessel, by means of radiation and of a detector (3) receiving radiation while the vessel moves along with a rotor revolving around the vertical axis (15) of a centrifuge. Thereby the beam of measurement (5) coming from the source of radiation (1) passes substantially horizontally and the intensity of the radiation passing through, or reflected from, the contents of the vessel is measured. According to the invention, for the purpose of the measurement of the properties of the liquid, after the vessel (2) has pivoted for the measurement by the effect of centrifugal force so that its longitudinal axis is positioned substantially horizontally, a field of limited area is measured out of the bottom of the vessel (2) while the vessel (2) moves along with the rotor of the centrifuge through the space between the source of radiation (1) and the detector (3). The measurement result of the component field at each particular time under measurement is read constantly or at specified intervals for the purpose of processing and output of the information.

15 Claims, 8 Drawing Figures pos.

neg.

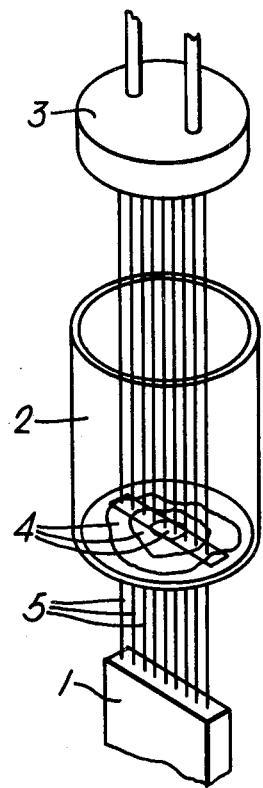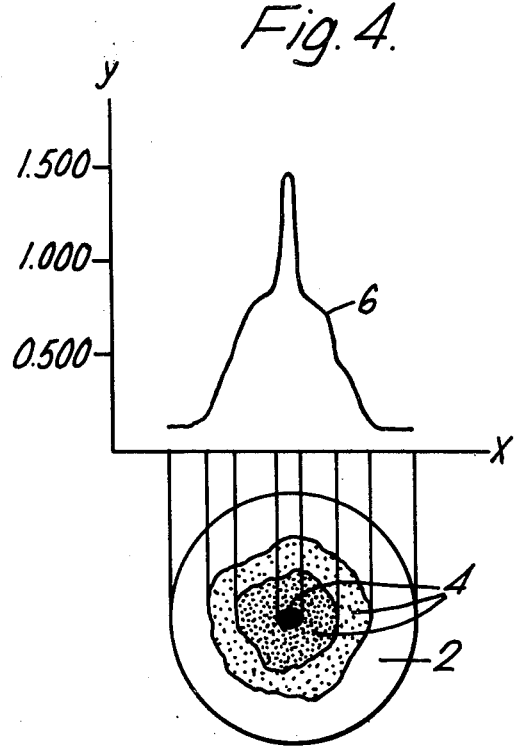

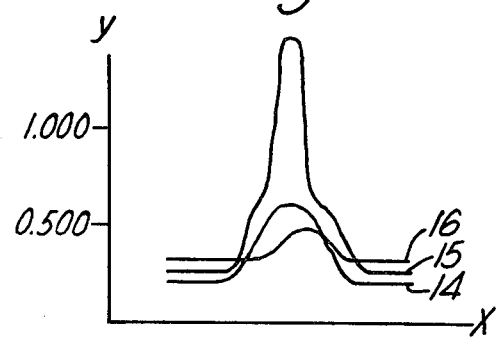
Fig. 5.
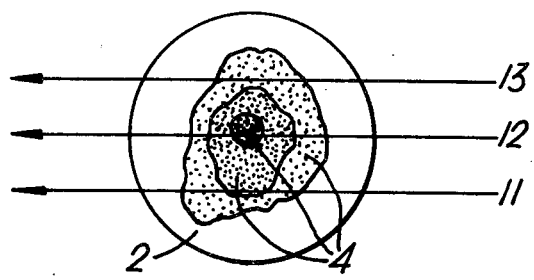
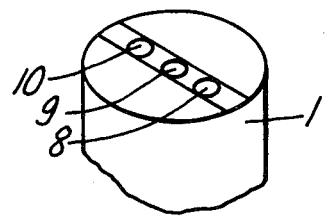
Fig. 6.

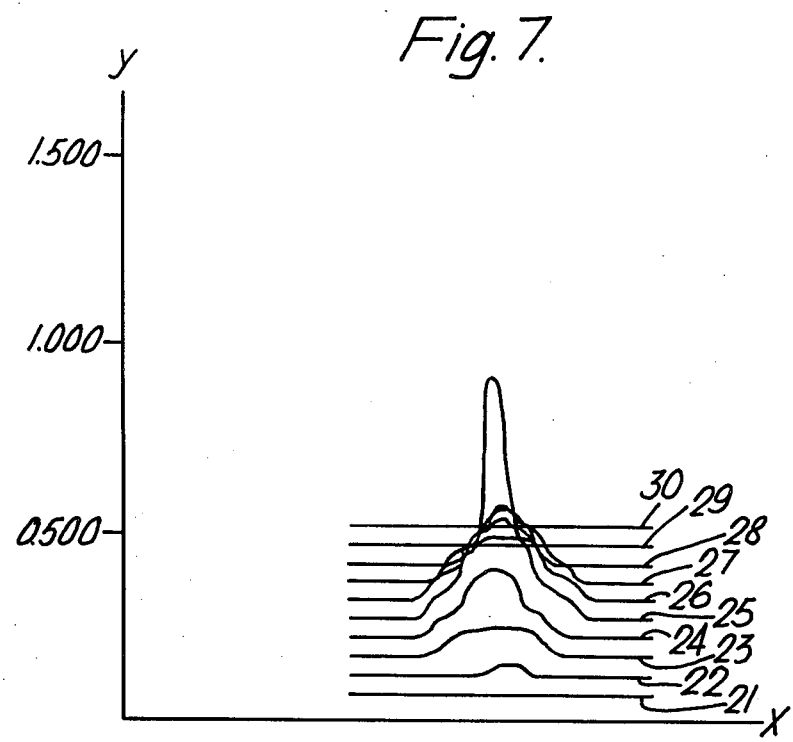
Fig. 7.
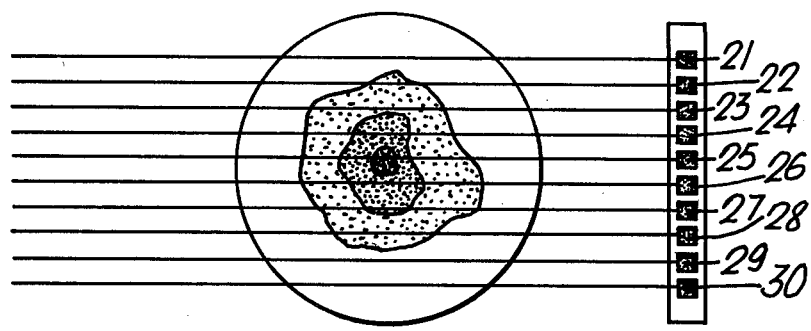

METHOD AND EQUIPMENT FOR THE MEASUREMENT OF PROPERTIES OF A LIQUID

BACKGROUND OF THE INVENTION

The present invention is concerned with a method for the measurement of properties of a liquid present in a vessel, for example for the measurement of the absorbance of a liquid, of the properties of an agglutination, precipitate or any other reaction result placed on the bottom of a vessel, by means of radiation and of a detector receiving radiation while the vessel moves along with a rotor revolving around the vertical axis of a centrifuge, the beam of measurement coming from the source of radiation passing substantially horizontally and the intensity of the radiation passing through, or reflected from, the contents of the vessel being measured. The invention is also concerned with an apparatus for the implementation of the method, which apparatus comprises a rotor revolving around a vertical axis, to which rotor the vessel can be fitted, one or several detectors receiving radiation and fitted so that the beam of measurement received by the detector(s) passes substantially horizontally, as well as an output unit.

Various tests based on agglutinations are in common use, blood-group identifications, antibody determinations, and rheumatic-factor measurements. In blood-group analytics and in antibody determinations the agglutination of red blood cells is concerned. The rheumatic factor is commonly measured by means of the agglutination of latex particles.

It has been customary to read the results of agglutination reactions visually. An experienced reader is also quite skilful in distinguishing between agglutination and non-agglutination. Such a mode of output is, however, quite subjective, and this is why the result is not always completely reliable. In clear situations with strong agglutination, visual reading is certainly no problem, but weak reactions of agglutination are often problematic. Among agglutination reactions, most difficult to interpret is a weak Rh-positive result obtained in blood-group identifications. In such situations it is of essential importance to obtain a reliable output, because the safety of the patient is concerned.

OBJECT OF THE INVENTION

The objective of the method in accordance with the invention (observation of reactions such as agglutination reactions and reading of the final results) is to enable the reader to ascertain the difference between agglutination and non-agglutination sufficiently clearly, reproducibly, and carefully. By means of the principle of vertical measurement (Suovaniemi, Osmo, "Performance and Properties of the Finnpipette Analyzer System", *Proceedings of the Second National Meeting on Biophysics and Biotechnology in Finland,* 183, 1976) it is possible to measure agglutination reactions. However, in the case of very weak agglutinations, one beam of light does not produce a sufficient difference in absorbance between agglutination and non-agglutination. In the method in accordance with the invention any uncertainty is eliminated by performing the measurement of the properties of the agglutination precipitate at several points once or several times so as to observe the formation of the precipitate as a function of time.

The agglutinated precipitate formed on the bottom of the reaction vessel is structurally different from a non-agglutinated precipitate. The former is unhomogeneous, at the middle part denser than at the sides, whereas the latter is even and relatively homogeneous. By performing the measurement of absorption of light at several different points of the precipitate obtained, it is possible to distinguish between agglutinated precipitate and non-aggulatinated precipitate reliably.

SUMMARY OF THE INVENTION

The method in accordance with the invention peforms the measurement of the properties of the liquid, after the vessel has pivoted for the measurement by the effect of centrifugal force so that its longitudinal axis is positioned substantially horizontally. A field of limited area is measured out of the bottom of the vessel while the vessel moves along with the rotor of the centrifuge through the space between the source of radiation and the detector, and the measurement result of the component field at each particular time under measurement is read constantly or at specified intervals for the purpose of processing and output of the information.

In the apparatus in accordance with the invention at one time, either the source of radiation or the detector receiving radiation covers only a limited component field of the bottom of the vessel. In various embodiments the source of radiation or the detector receiving radiation may be a narrow, vertical slit placed outside the circle formed by the course of movement of the bottom of the reaction vessel; or either may be point-shaped and placed outside the circle formed by the course of movement of the bottom of the reaction vessel and displaceable in the vertical direction during the revolutions of the centrifuge; or either may be point-shaped and two or more of them have been fitted in a vertical line, and that, when several sources of light are used in a line, each source of light is in operation alternatingly.

In this method the measurement of the precipitate or any other type of reaction product produced is accomplished at several points in the following way. The reaction vessel is placed in a frame or holder which is fastened to the rotor of the centrifuge so that the vertical axis of the reaction vessel is during rotation of the rotor pivoted to the horizontal plane. The beam of measurement then passes in the direction of the vertical axis of the reaction vessel, which has been pivoted to the horizontal position. Outside the circle along which the bottom of the reaction vessel travels the source of light is placed, which is either point-shaped or of the shape of a vertical slit and whose light is directed at the centre of rotation of the rotor. Inside the circle along which the mouth of the reaction vessel passes, the detector is placed so that the light coming from the said source of light falls on the detector. When the rotor rotates, the reaction vessel by-passes the beam of measurement, whereby the various parts of the precipitate placed on the bottom of the reaction vessel pass at a high speed of revolution through the beam of measurement. The detector registers the absorption of light at different points of the precipitate as a function of time as the precipitate by-passes the source of light, and the electronics fitted into the apparatus decide whether the precipitate is agglutinated or not, based on the registered line of light absorbance values.

Some of the features typical of the apparatus based on the method described above are as follows:

1. Therein a modified principle of vertical measurement is applied, wherein the beam of measurement is parallel to the centrifugal acceleration.

2. The reaction vessel is placed on a pivoting holder of the rotor of the centrifuge, and it is pivoted so that, when the rotor rotates, the longitudinal axis of the vessel is horizontal and parallel to the readius of the rotor.

3. The horizontal beam of measurement is directed towards, or away from, the centre point of the rotor in the direction of the radius of the rotor so that, when rotating, the reaction vessel by-passes the beam.

4. The detector registers the absorption of light at subsequent points of the precipitate placed on the bottom of the reaction vessel rapidly and in the way determined by the control electronics.

5. The apparatus may also be applied to the measurement of phenomena other than absorption of light, e.g., to the measurement of fluorescence, luminescence, etc.

DESCRIPTION OF THE DRAWING

The invention will be described in more detail below with reference to the attached drawings, wherein FIG. 4 shows an absorbance curve obtained from the reaction vessel of FIG. 1; underneath the curve, the reaction vessel of FIG. 1 is shown as viewed from the top (in the curves of the figures, the x-axis illustrates the location of the point of measurement on the path of movement and the y-axis illustrates the absorbance at each particular time or in each particular point), FIG. 5 shows absorbance curves obtained by means of the source of light shown in FIG. 6; underneath the curves the precipitate measured is shown as viewed from above, FIG. 6 is a schematical perspective view of a source of light that consists of several point-shaped surces of light, and FIG. 7 shows absorbance curves, underneath which a top view of the precipitate measured and the detector used are illustrated.

DETAILED DESCRIPTION OF THE PREFERRED EMBODIMENT

Figure 1A:
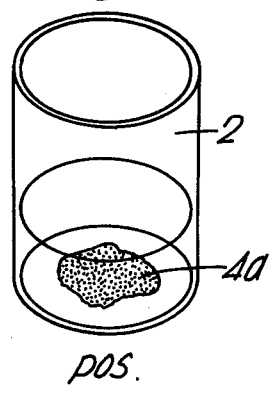
FIGS. 1a and 1b show two different precipitates.
Figure 1B:
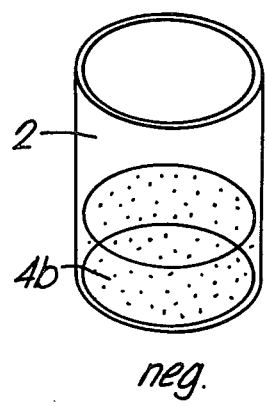

In FIG. 1a there is a precipitate 4a on the bottom of the reaction vessel 2, the shape and density of the said precipitate being at different points different from those of the precipitate 4b shown in FIG. 1b. The precipitate 4a illustrates an agglutinated situation, whereas FIG. 4b represents a non-agglutinated precipitate in the situation of measurement.

Figure 2:
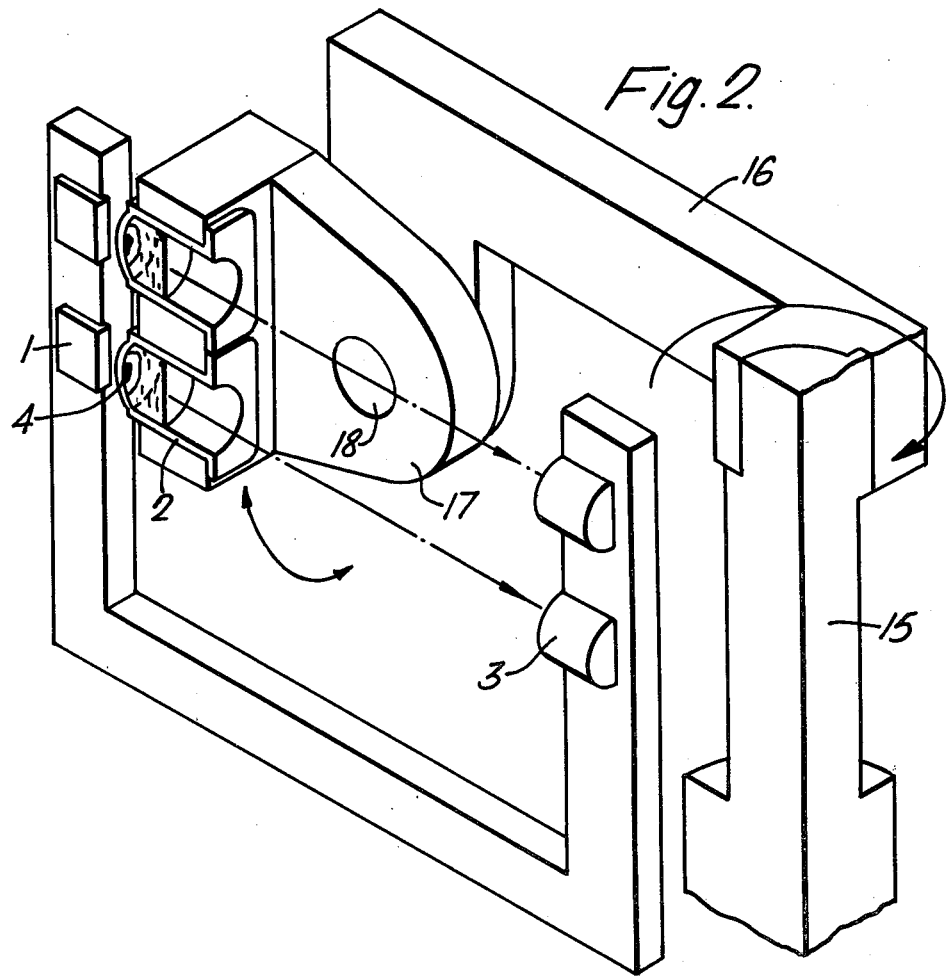
FIG. 2 is a schematical and partly sectional presentation of an apparatus in accordance with the invention, FIG. 3 schematically shows an alternative in which one slit-shaped source of light is used that can be shifted in relation to the reaction vessel.

FIG. 2 shows the shaft 15 of rotation of the centrifuge, a rotor arm 16 connected to the shaft, as well as a holder 17, connected to the arm as pivotable around a horizontal shaft 18, the said holder being provided with two reaction vessels 2 in the horizontal position that is assumed by them when the rotor rotates. The light departing from the slit-shaped sources of light 1 passes through the reaction results, e.g. precipitate 4, placed on the bottom of the reaction vessels 2 and reaches the detectors 3, which, during rotation of the rotor of the centrifuge, register the absorption of light of the precipitate 4 at different points of the precipitate.

FIG. 3 schematically shows a slit-shaped source of light 1, a reaction vessel 2, and a detector 3. The length of the slit is preferably somewhat less than the diameter of the vessel bottom. On the bottom of the reaction vessel 2 there is a precipitate 4, which has layers of different types and thicknesses. When the reaction vessel 2 passes across the stationary source of light 1 and detector 3 once in the transverse direction of the slit 1 so that the slit-shaped beam of light 5 passes, point by point, through the precipitate 4 on the bottom of the reaction vessel 2, the absorbance curve 6 shown in FIG. 4 is obtained, which curve may be continuous or consist of individual points.

FIG. 4 also shows a top view of the precipitate 4 on the bottom 2 of the reaction vessel. The measurement has been performed by instantaneously measuring a vertical stripe of the shape of the slit-shaped source of light out of the precipitate on the bottom of the reaction vessel and by producing the output of the measurement value of this stripe. The production of the output may take place for each stripe separately, whereby a stepwise curve or a curve consisting of individual points is obtained, or as a continuous measurement, whereby the detector measures constantly during the movement and a continuous curve is obtained as the result.

FIG. 5 shows a precipitate measured from the bottom of the reaction vessel so that the reaction vessel has passed across the point-shaped sources of light 8 to 10 shown in FIG. 6 so that measurement has first been performed by means of the source of light 8 and the other beams 9 and 10 have been closed. During the next revolution of the rotor the measurement has been performed by means of the beam 9, and the beams 8 and 10 have been closed. Finally, the beams 8 and 9 have been closed, and the measurement has been performed by means of the beam 10. In FIG. 5, the beam 10 corresponds to scan 13 and the absorbance curve 16. Correspondingly, the beams 9 and 8 correspond to scans 12 and 11 and the absorbance curves 15 and 14 respectively. It is also natural that the point-shaped source of light may move along the slit shown in FIG. 6, being alternatingly in positions 8, 9 and 10.

In FIG. 7 it is shown how a detector placed outside the rotor may consist of several sub-detectors 21 to 30 mounted in a vertical line, the said sub-detectors registering the light coming from the source of light placed inside the rotor and through the precipitate placed on the bottom of the vessel, each of them at a height of its own. In this way highly abundant information is obtained from the precipitate placed on the bottom of the reaction vessel. Of course, each detector may also consist of several separate sub-detectors positioned in a matrix form, whereby a complete topography is obtained from the reaction during each revolution. It is also natural that the evolution of the topographic result may be observed as a function of time, whereby different topographies in relation to time mean different final results.

The invention is not confined to the above alternative embodiments alone, but it may show even considerable variation within the scope of the patent claims.

It is evident that in the method described above the source of light and the detector may change places, whereby the detector is placed outside the circle of the rotor and the source of light inside. In such a case the detector must be correspondingly given the shape of a point or of a vertical slit.

In this method there may be several reaction vessels on the circumference of the same rotor, in which case the results are registered subsequently from one vessel after the other in the way described above and the apparatus is provided with electronics capable of sorting and arranging the readings.

It is also possible to design the holders for reaction vessels on the rotors so that a matrix of vessels consisting of several individual reaction vessels can be placed on each holder, e.g. a martix of the type used as a cuvette set in the FP-9 photometer (U.S. Pat. No. 4,144,030). In such a case the apparatus may be constructed as a multi-channel apparatus so that it is provided with several beams of measurement of the type described above, one beam above the other, at the heights corresponding the reaction vessels.

If a point-shaped source of light or detector is used, it is possible to allow it to move in the vertical direction so that, during the movement of rotation, the beam of measurement passes through the precipitate on the bottom of the reaction vessel at several points, during each subsequent revolution of the rotor slightly higher or lower. In this way it is possible to assemble abundant information on the shape and structure of the precipitate, and thereby to decide more certainly whether it is agglutinated or not. By means of the measurement it is possible to assemble information on the evolution of the precipitate as a function of time, on its location, shape, and/or on the density of its various points.

The method of measurement may be based on photometry or multiphotometry, the latter meaning a photometer which comprises several channels so that each sample has a source of light and a detector of its own.

the method of measurement of the present invention may also be based on turbidometry or fluorometry, or may employ luminescence, laser beam, ultrasound, or other measurement beams either singly or combined in a multi-channel method.

The positioning of the reaction vessels or equivalent, of sources of measurement beams, of detectors, or auxiliary equipment may be performed in the way most appropriate in each particular case. The equipment may also involve various degrees of automation, in the pipetting of the samples and reagents, in the shifting of the beams of measurement, and in the processing of the results. It is natural that, in stead of one method of measurement, the reaction vessels may be measured simultaneously or subsequently by means of two or more wave lengths or methods of measurement (e.g., photometry and fluorometry), the final result being based on the information thereby obtained.

The invention permits, other measurements such as enzyme and end-point measurements in the reaction vessel. In the case of enzyme measurements it is possible to observe the progress of the reaction at certain time intervals, and the final result is determined from the measurement values in this way obtained.

What is claimed is:

1. A method for the measurement of properties of any precipitated reaction product which might be contained within a solution to be tested and which appears on the bottom of a vessel while said vessel is revolving on a centrifuge comprising:

placing a vessel which contains said solution on a centrifuge;

rotating said centrifuge so that said vessel is pivoted to a substantially horizontal position by the action of centrifugal force and matter suspended in said solution is caused to precipitate;

passing a substantially horizontal beam of radiation along a longitudinal axis of said vessel which beam passes through a field of limited area out of the bottom of said vessel, said vessel intersecting said beam on its path about said centrifuge;

detecting said beam of radiation at different points of said vessel bottom as said beam passes through said vessel on repeated rotations over time;

reading the intensity of said detected radiation to obtain a measurement at each particular time; and processing said measurements to determine the properties of any precipitate present in said solution as well as any change in said properties as a function of time.

2. The method of claim 1 wherein said reading step is carried out continuously throughout said method.

3. The method of claim 1 wherein said reading step is carried out at specified intervals.

4. The method of claim 1 wherein said field of limited area is a narrow vertical stripe.

5. The method of claim 1 wherein said measurements are graphically displayed as a curve on a set of (x)-(y) axes where for each coordinate the (x) value represents the position of the field so measured on the bottom of the vessel and the (y) value represents the measurement value obtained in that region of the bottom of the vessel.

6. The method of claim 1 wherein said field of limited area is a point-shaped field whose position in the vertical direction is changed during the revolutions of the centrifuge.

7. The method of claim 1 wherein the field of limited area is a vertical line having at least two point shaped fields as components thereof.

8. The method of claim 7 wherein at least two point shaped fields are measured and said measurements are graphically displayed to generate a corresponding number of curves on a set of x-y axes where for each coordinate the (x) value represents the position of the field on the bottom of the vessel and the (y) value represents the measurement value obtained in that region of the bottom of the vessel.

9. An apparatus for the measurement of the properties of a liquid which comprises:

a rotatably mounted vertical axis;

a rotor which is mounted on said vertical axis;

means for rotating said rotor about said vertical axis;

a vessel pivotally attached to said rotor in a vertical resting position such that said vessel may be pivoted into a horizontal measuring position by centrifugal force when said rotor rotates;

a source of radiation which projects a beam of radiation along a radius of the circle described by the course of movement of the bottom of the vessel and is aligned so that said beam of radiation passes through the vessel as its path of rotation intersects the beam, said beam of radiation covering only a limited, selectable component field of the bottom of the vessel;

a detector means positioned on said radius to receive the radiation from said beam of radiation which emerges from said vessel to provide measurement signals; and means for processing measurement signals generated on repeated passes of the vessel through said beam through plural limited component fields.

10. The apparatus of claim 9 wherein the source of radiation is a narrow vertical slit placed outside the circle formed by the course of movement of the bottom of the vessel.

11. The apparatus of claim 9 wherein the source of radiation is point-shaped and placed outside the circle formed by the course of movement of the bottom of the vessel and displaceable in the vertical direction during the revolutions of the rotor.

12. The apparatus of claim 9 wherein the detector means is point-shaped and placed outside the circle formed by the course of movement of the bottom of the vessel and displaceable in the vertical direction during the revolutions of the rotor.

13. The apparatus of claim 9 wherein the source of radiation is two or more point-shaped sources fitted in a vertical line, said point sources being alternately operative.

14. The apparatus of claim 9 wherein the detector means is two or more detectors disposed in a vertical line.

15. The apparatus of claim 9, wherein a plurality of vessels may be fitted to the apparatus and several detector means and sources of radiation aligned at the various levels of the rotor corresponding to the vessels.

* * * * *